United States Patent [19]

Wang

[11] Patent Number: 4,621,049

[45] Date of Patent: Nov. 4, 1986

[54] ENZYMATIC HIGH RANGE GLUCOSE TEST

[75] Inventor: Joseph Y. Wang, Elkhart, Ind.

[73] Assignee: Miles Laboratories, Inc., Elkhart, Ind.

[21] Appl. No.: 673,183

[22] Filed: Nov. 19, 1984

[51] Int. Cl.$^4$ ............................................. C12Q 1/54
[52] U.S. Cl. ......................................... 435/14; 427/2; 435/805
[58] Field of Search ........................ 435/14, 25, 805; 436/95; 422/56, 57; 427/2

[56] References Cited

U.S. PATENT DOCUMENTS

| | | | |
|---|---|---|---|
| 2,912,309 | 11/1959 | Free | 435/14 |
| 3,630,957 | 12/1971 | Rey et al. | 436/95 X |
| 3,814,668 | 6/1974 | Blake et al. | 435/14 |
| 3,964,870 | 6/1976 | Tiedemann et al. | 435/14 |
| 4,288,541 | 9/1981 | Magers et al. | 435/14 |
| 4,303,753 | 12/1981 | Lam | 435/14 |
| 4,312,834 | 1/1982 | Vogel et al. | 422/56 |
| 4,340,669 | 7/1982 | Bauer | 436/95 X |

OTHER PUBLICATIONS

Fujisawa, Chemical Abstracts, vol. 96, 1982, No. 96:196173h.

Primary Examiner—Arnold Turk
Attorney, Agent, or Firm—Mary G. Boguslaski

[57] ABSTRACT

A test composition comprising glucose oxidase, a peroxidatively active component, a chromogenic indicator system capable of providing a detectable response and a borate buffer capable of providing an initial pH above about pH 7 is particularly useful for the semiquantitative determination of high range glucose, (i.e. glucose concentrations of 1,000 mg/dL to 10,000 mg/dL). A preferred indicator system is a water soluble iodide salt and poly(vinylpyrrolidone). The use of a borate buffer capable of providing an initial pH above about pH 7 permits greatly improved resolution for the semiquantitative determination of high range glucose when the test composition is incorporated onto a carrier matrix to prepare a solid state unitary test device.

12 Claims, No Drawings

ENZYMATIC HIGH RANGE GLUCOSE TEST

FIELD OF THE INVENTION

The present invention relates to enzymatic diagnostic compositions in general and to the semiquantitative enzymatic determination of high range glucose in aqueous fluids in particular.

UTILITY

The semiquantitative determination of glucose in body fluids, such as urine or blood, is of importance as a public health measure to screen the urine or blood of large numbers of people for diabetes and is of particular importance for diabetic patients who must control their sugar intake. Because early diagnosis and continued control are so important in diabetes, a glucose test, to be of greatest value to the physician, clinician or home diabetic user must be rapid and simple enough to perform conveniently and yet sensitive enough to reflect meaningful variations in urine or blood glucose. Semiquantitative determination of high range urine glucose concentration, concentrations over 1,000 milligram per deciliter (mg/dL), is important because urine glucose concentration in diabetic patients can be as high as 5,000 mg/dL or even higher. The semiquantitative estimation of high range of glucose, "high range" defined herein for convenience as a glucose concentration of 1,000 mg/dL to 10,000 mg/dL or above, is important for at least two reasons: (a) to aid in differential diagnosis between diabetic coma and other drug, alcohol or injury induced coma, and (b) as an aid in therapeutic monitoring of insulin requirement. In emergency situations, a test indicating very high glucose levels would suggest a diabetic coma. Since urine glucose levels become elevated if an insufficient amount of insulin has been administered, a test which can semiquantitatively determine high range glucose therefore has utility in the therapeutic monitoring of insulin requirement.

INFORMATION DISCLOSURE

Most diagnostic testing for glucose performed clinically is based on the enzymatic action of glucose oxidase on β-D-glucose:

$$H_2O_2 + \text{gluconic acid} + O_2 + H_2O$$

and the resultant oxidation of a chromogen (Cr) to its oxidized state (Cr*) which is visually detectable by a color change:

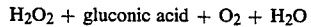

The greatest convenience is obtained when the test device can be used to semiquantitatively determine glucose concentration levels by visual comparison of the color developed after contact with a test sample with an appropriate color chart. Such semiquantitative determinations can also be performed instrumentally by measuring the reflectance of a reacted test device. Early patents such as U.S. Pat. Nos. 2,848,308 and 2,912,309, assigned commonly herein, each disclose a glucose test "stick" wherein a stick coated with a gelatin solution was dipped into a fine powder mixture containing glucose oxidase, peroxidase, o-tolidine, dihydrochloride and boric acid. Boric acid constitutes approximately 75% by weight of the mixture and the patents state that the boric acid can be substituted by any other "filler" such as talc, starch, sodium citrate-citric acid mixtures, titanium oxide, silica gel and the like. The glucose stick so prepared turned blue when moistened with a liquid containing glucose.

Since then, many variations in the components of an enzymatic glucose test composition have been made to improve the semiquantitative discrimination between different concentrations of glucose. However, in many improved systems as the concentration of glucose increases above 500 mg/dL the color of the chromogen is so dark as to preclude distinguishing between high range glucose concentration levels. British Pat. Spec. No. 1,464,359 describes the results observed with o-tolidine, tetramethylbenzidine and tetraethylbenzidine as the chromogen when aqueous test samples containing 0, 50, 100, 250, 500 and 1,000 mg/dL glucose were tested. Each of these chromogens turns from yellow to bright green when the concentration of glucose increases from 0 to 50 mg/dL. As the concentration of glucose increases above 500 mg/dL the color of the oxidized chromogen darkens so that the observed colors of the respective chromogens are olive-black, black and deep green, respectively. This observation highlights a problem with semiquantitative glucose determinations at high concentrations i.e., known chromogens appear black or very dark green thereby limiting the utility of the test devices for determinations of glucose above 500 mg/dL. While the problem is not so acute if the color change is determined instrumentally it nonetheless still exists.

The U.S. Pat. No. 4,340,669 patent also describes some success in expanding the glucose concentration range which can be visually determined with an enzymatic glucose test device by the addition of a secondary chromogen such as manisidine. Adequate quantitation for mid-range glucose (i.e. between 500 mg/dL and 1,000 mg/dL) can be obtained with a glucose oxidase formulation utilizing water soluble iodide salt and a poly(vinylpyrrolidone) as a chromogen as disclosed in U.S. Pat. No. 4,303,753.

Complexation of sugars with boric acid or its derivatives has been reported [see S. A. Barker et al., *Carbohydrate Research* 26, (1973) 33–40]; however, to the applicant's knowledge, this phenomenon has not been used to solve the problem of determination of high range glucose in aqueous test samples.

SUMMARY OF THE INVENTION

The invention provides a test composition, a test device and method for the semiquantitative determination of high range glucose in an aqueous test sample comprising glucose oxidase, a peroxidatively active component, a chromogenic indicator system capable of providing a detectable colorimetric response and a borate buffer capable of providing an initial pH above about pH 7. High range glucose is defined herein as glucose concentrations of from about 1,000 mg/dL to about 10,000 mg/dL. The composition can be incorporated with a carrier matrix to provide a solid state test device. High range glucose can be determined visually or instrumentally in less than 5 minutes, preferably in about 2 minutes. The invention is particularly advantageously used for the semiquantitative visual determination of high range glucose.

DETAILED DESCRIPTION OF THE INVENTION

It has been found that a glucose oxidase test composition including a borate buffer capable of providing an initial pH above about pH 7 is useful for the semiquantitatively determination of high range glucose in an aqueous test sample. A particularly convenient test format can be prepared by incorporating a carrier matrix with the composition to form a solid state test device. Although the preferred application is to the testing of body fluids such as blood, serum, plasma, urine, spinal fluids, it should be understood that the disclosed composition, test device and method can be used with aqueous solutions of industrial interest as well.

While many buffers including citrate, phosphate, N,N'-Bis(2-hydroxyethyl)glycine and N-2- hydroxyethylpiperazine have been used with a glucose oxidase/peroxidase system in experimental efforts to obtain increased resolution for high range glucose, a borate buffer capable of providing an initial pH above about pH 7 was the only buffer system which provided such greatly improved resolution between high range concentration levels of glucose.

1. Test Components

While glucose oxidase compositions such as that disclosed in U.S. Pat. No. 4,303,753 provide adequate semiquantitative determination of glucose concentrations between 500 and 1,000 mg/dL, the substitution of a borate buffer capable of providing an initial pH above about pH 7 for previously used buffer conditions greatly improved the semiquantitative determination of high range glucose, i.e., concentration levels in the range from about 1,000 mg/dL to about 10,000 mg/dL.

A borate buffer is defined as a mixture of the acid and base form of Z-B(OH)$_2$. The equilibrium can be shown schematically as:

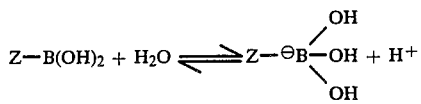

where the Z radical can be an hydroxyl group (—OH) or any electron withdrawing substituent. For example where Z is the hydroxyl group the compound is boric acid [B(OH)$_3$]. Where Z is a phenyl group, the compound is phenylboronic acid. Suitable boron dihydroxides include boric acid, phenylboronic acid, p-nitrophenylboronic acid, 4-methoxyphenylboronic acid as well as other areneboronic acids and their derivatives. Arene groups, defined as any hydrocarbon containing at least one aromatic ring, are examples of electron withdrawing groups which can be used as the Z substituent in the present invention provided the aromatic ring is placed relative to the —B(OH)$_2$ radical in such a way as to allow electron resonance to stabilize the anionic form. Arene derivatives also containing electron withdrawing groups as substitutents on the aromatic ring, such as p-nitrophenylboronic acid, are also useful in the present invention.

The borate buffer can be prepared from boric acid (Z=OH) or from areneboronic acid derivatives such as phenylboronic acid or mixtures of Z-B(OH)$_2$ compounds by commonly used laboratory methods well known to those skilled in the art. For example, a solution of boric acid buffer can be prepared by titrating boric acid with a base such as sodium or potassium hydroxide to an initial pH above pH 7. When a boric acid buffer is used, the initial pH is preferably between about 8.5 and about 9.5. For use in a dry test composition the water can be removed from the buffer solution leaving a powder capable of providing the desired initial pH when reconstituted for use.

Suitable chromogenic indicator systems for use in the present invention include poly(vinylpyrrolidone) with water soluble iodide salts and 4-aminoantipyrine with suitable couplers such as dichlorohydroxybenzene sulfonic acid; 4-methylcatechol; 2,4-dihydroxybenzoic acid and 3,6-dihydroxynapthalene-2,7-disulfonic acid. Poly(vinylpyrrolidone) can be obtained from GAF Corp., New York, N.Y. in a number of different average molecular weights for example PVP-K15, (average molecular weight 10,000), PVP-K30 (average molecular weight 40,000), PVP-K60 (average molecular weight 160,000) and PVP-K90 (average molecular weight 360,000). A preferred indicator system is a water-soluble iodide salt with a poly(vinylpyrrolidone); most preferably the high molecular weight poly(vinylpyrrolidone), PVP-K90. Suitable water soluble iodide salts include barium iodide, potassium iodide, sodium iodide, ammonium iodide and tetraalkyl ammonium iodide. The iodide salt must be ionizable, and the cationic portion of the salt must not interfere with the enzymatic catalysis of the glucose oxidation. Of the suitable iodide salts, economic considerations and availability suggest that potassium iodide is a particularly preferable salt in the present invention.

Glucose oxidase (E.C.1.1.3.4) can be obtained from Miles Laboratories, Inc., Elkhart, IN., or Sigma Chemical Co., St. Louis, MO. Substances having peroxidative activity which are useful in the present invention can be chosen from various organic and inorganic sources. Plant peroxidases (EC 1.11.1.7), such as horseradish peroxidase or potato peroxidase, can be used. In addition, even though less satisfactory, hemin and hemin derivatives, hemoglobins and hematin can be used.

Additional components such as wetting agents, stabilizers or thickeners can be added provided they do not interfere with the production of a detectable response. Suitable wetting substances include N-lauroylsarcosine which can be obtained under the trademark Sarkosyl ® from Sigma Chemical Co., St. Louis, MO.; Emulphor ® ON 870, a trademark preparation of polyoxyethylated oelyl alcohol sold by GAF Corp., New York, N.Y. and Triton ® X-100, a registered trademark of the Rohm and Haas Co. for polyethyleneglycol-p-isooctylphenyl ether which can also be obtained from Sigma Chemical Co. The use of these components to prepare test devices is well known and the choice therefore is well within the ability of one of ordinary skill in the art.

The test composition can be provided in the form of a bottled reagent, frangible capsule containing the test composition in reagent form, a pill or a tablet.

2. Carrier Matrix

A preferred form of the invention is prepared by treating a suitable carrier matrix with the test composition in the form of a aqueous reagent mixture.

The carrier matrix can be any substance capable of being incorporated with the components of the test composition, as long as it is substantially inert with respect to the test composition, porous and/or absorbent relative to the aqueous sample to be tested. The expression "carrier matrix" refers to either bibulous or nonbibulous matrices which are insoluble in and maintain their structural integrity when exposed to water or to other physiological fluids. Suitable bibulous matrices which can be used include paper, cellulose, wood, synthetic resin fleeces, woven and nonwoven fabrics and the like. Suitable non-bibulous matrices which can be used include glass fiber, polymer films and microporous membranes.

It is, therefore, to be appreciated that in producing a test device of the invention all such carrier matrix concepts can be employed, as can others. The matrix can also comprise a system wherein the composition ingredients are homogeneously combined in a fluid or semi-fluid state, which later hardens or sets, thereby incorporating the ingredients. Other matrix formats are contemplated, including the use of a microporous membranes or polymer film matrices. Microporous membranes are available as preformed membranes or can be prepared by such techniques as phase inversion. Suitable polymer films can be produced with commercially available latex formulations based on latex polymer suspensions, for example that formed by a 60:40 copolymer of styrene and butadiene. Other natural or synthetic polymers or mixtures thereof can also be used. Examples of such film formulations can be found in U.S. Pat. Nos. 3,630,957 and 4,312,834, incorporated herein by reference.

3. Test Device

Preferably, the test device is prepared by incorporating the carrier matrix with the test composition with drying.

The presently preferred method is impregnating a bibulous carrier matrix, for example filter paper, with an aqueous solution of the composition and drying, followed by affixing the dried impregnated matrix to a support member. The impregnating solution is prepared so that it exhibits the desired initial pH. When a whole blood sample is to be tested, the dried impregnated carrier matrix can be coated to allow excess sample to be washed or wiped off. Drying can be accomplished by any means which will not deleteriously affect the incorporated composition, usually by means of an air oven. Incorporation can be accomplished by any method such as coating, dipping, spreading, spraying or printing which allows the carrier matrix to be incorporated with the test composition. The dried carrier matrix can thereafter be cut and mounted on one end of a support member, for example, a rigid or semirigid polystyrene film strip. Mounting of the dried carrier matrix on the support can be accomplished through use of double-faced adhesive tape, such as that commercially available from the 3M Co., St. Paul, Minn., under the trademark DOUBLE STICK ®.

4. Concentration Ranges of Test Components

Concentration ranges for components in the reagent solution used to prepare a solid state test device are as follows:

|  | working | preferred |
| --- | --- | --- |
| glucose oxidase | 300 to 5000 U/mL | 2000 to 3000 U/mL |
| peroxidase | 200 to 5000 U/mL | 1000 to 2000 U/mL |
| borate buffer | 0.2 to 0.8M | 0.5 to 0.8M |
| initial pH | 7 to 10 | 8.5 to 9.5 |
| indicator system |  |  |
| PVP-K90 | 0.1 to 5.0% | 0.5 to 1.0% |
| KI | 0.05–1M | 0.1 to 0.2M |

It is particularly preferred to utilize as high a borate concentration as possible (i.e., 0.7 M to about 0.8 M) at an initial pH of from about 9.0 to about 9.1. The reagent solution is used to incorporate the test composition into a carrier matrix. The borate buffer provides the preferred initial pH. After the carrier is dried, the buffer is capable of providing the preferred initial pH when the surface of the device is wetted. This surface pH can be defined by means of a surface electrode.

These concentration ranges and relative concentrations of components are viable whether the solution is an aqueous solution as used to impregnate a paper carrier matrix or an aqueous polymer suspension used to form an polymer film incorporated with the test components.

When a paper carrier matrix is used, the paper can be pretreated with a borate buffer at an initial pH above about pH 7, such as phenylboronic acid buffer, prior to incorporation of a test composition containing a borate buffer. It is speculated that such a pretreatment prevents possible interaction of the paper matrix with the borate buffer in the test composition.

5. Method of Use

The test device is advantageously used by momentarily dipping it in a test sample or by otherwise introducing a test sample onto the carrier matrix, whereby a detectable colorimetric response results when 500 mg/dL glucose or greater is present. Contact with the test sample can also be made by pipette, swab or spatula. Although dipping is a highly satisfactory method of contact when urine is used, a serum sample will normally require pipetting.

Semiquantitative glucose concentrations can be determined visually by comparison with an appropriate color chart or instrumentally by measuring the reflectance of a reacted test device. Measurements can be made from either side of the device if a transparent support member is used.

The following examples describe experiments which were performed in developing the present invention. While the examples serve to illustrate the invention, they are not to be interpreted as limiting its scope which is defined solely by the claims. One skilled in the art will be able to make such variations, substitutions and changes in the components of the composition and ingredients and reaction parameters as may seem desirable.

ABBREVIATIONS

The following abbreviations are used in the Examples for convenience.

| | |
| --- | --- |
| mL | milliliter |
| dL | deciliter |
| gm | gram |
| M | molar |
| °C. | degrees centigrade |
| POD | peroxidase |
| GO | glucose oxidase |
| DHSA | dichlorohydroxybenzenesulfonic acid |
| Poly (ST-Co-MAA) | Styrene and methylmethacrylate copolymer |
| FC&D #5 | yellow dye, color index number 19140 |
| PVP-K90 | poly(vinylpyrrolidone), average molecular weight 360,000 from GAF Corp., New York N.Y. |
| Sarkosyl ® | a surfactant, N— |

|   |                                                                                                                                                                                   |
| - | --------------------------------------------------------------------------------------------------------------------------------------------------------------------------------- |
|   | lauroylsarcosine, obtained from Sigma Chemical Co., St. Louis, MO.                                                                                                                |
| U | one International Unit (U) is of the amount of enzyme which catalyzes the conversion of 1 micromole of substrate per minute.                                                      |
| qs | to the volume of                                                                                                                                                                  |

EXAMPLES

EXAMPLE 1

Borate Buffer Formulation

Whatman 54 filter paper was dipped in an aqueous solution containing

| PVP K90 | 0.15 gm |
| --- | --- |
| GO | 50,000 U |
| POD | 24,000 U |
| KI | 0.6 gm |
| Sarkosyl | 0.1 mL |
| Boric Acid Buffer (1M, pH 8.7 adjusted with NaOH) | 14 mL |
| Water | qs. 20 mL |

Excess solution was removed by scrapper bars and the paper was dried at 50° C. for 20 minutes in an air oven. A double sided adhesive was applied to the dried reagent paper which was then slit into ribbons 1/5 inch wide. A ribbon was placed on one wide end of elongated pieces of polystyrene which was then slit into strips 1/5 inch wide forming test devices of the present invention.

The devices when dipped into aqueous test samples containing 0, 500, 1,000, 2,000, 3,000, 5,000 and 10,000 mg/dL glucose showed good visual resolution, 2 minutes after contact.

EXAMPLE 2

Comparison to an Optimized Nonborate Formulation

Test devices prepared according to Example 1 using a borate buffer were compared to an optimized glucose oxidase/peroxidase test formulation commercially available from Ames Division of Miles Laboratories, Inc., Elkhart, Indiana. The Diastix ® formulation contains a citrate buffer (pH 7.2) and a PVP/KI indicator. Each formulation was read at the optimum read time to maximize resolution between glucose concentration levels. The optimum read time for the borate formulation is 120 seconds while for the nonborate commercial formulation it is 30 seconds. At read times greater than this for either formulation the colors darken and therefore the differentiation between concentration levels decreases. In order to facilitate comparison between the formulations, the devices were read by reflectance measurement in a MacBeth 1500 colorimeter (Kallmorgen Corp., Newburgh, N.Y.).

These reflectance data were used to calculate the ΔE between two test devices after contact with samples containing different concentrations of glucose. ΔE is a measure of the total color difference between two devices in three-dimensional color space. ΔE is calculated with the following equation: [See D. B. Judd and G. Wyszecki, "Color in Business, Science and Industry", John Wiley and Sons, New York (1975)]

$$\Delta E = [(\Delta L^*)^2 + (\Delta a^*)^2 + (\Delta b^*)^2]^{\frac{1}{2}}$$

where $\Delta L^*$ is a measure of the difference in lightness between the two samples, and varies from 0 for absolute black to 100 for a perfect white; $\Delta a^*$ is a measure of the difference in redness-greenness between two samples; and $\Delta b^*$ is a measure of the difference in yellowness-blueness. The $L^*$, $a^*$, $b^*$ are calculated from the reflectance at wavelengths from 400–700 nanometers. For visual testing the difference between concentration levels defined on a color chart should be as great as possible to allow the human eye to distinguish between the colors produced. Two colors can be perceived as different by the human eye if the ΔE between them is one color unit different. Practically, however, ΔE between concentration levels should be 3 units or greater to assure that the colors can be distinguished. The greater ΔE between concentration levels the easier it will be for the human eye to distinguish those levels.

The citrate-PVP/KI formulation turns a greenish tan when contacted by an aqueous test sample containing 1,000 mg/dL glucose and becomes progressively browner as the glucose concentration in a test sample increases. The borate-PVP/KI formulation is yellow when contacted with 500 mg/dL glucose becomes progressively browner as glucose concentration increases.

| glucose concentration | ΔE between levels | |
| --- | --- | --- |
|  | citrate | borate |
| negative |  |  |
|  | −47 | −25 |
| 1,000 mg/dL |  |  |
|  | −1 | −14 |
| 2,000 mg/dL |  |  |
|  | −3 | −12 |
| 3,000 mg/dL |  |  |
|  | −2 | −13 |
| 5,000 mg/dL |  |  |
|  | −1 | −12 |
| 10,000 mg/dL |  |  |
| read time | 30 sec. | 120 sec. |

The ΔE value between concentration levels indicates that the borate formulation is much superior to the optimized commercially available citrate formulation for the determination of high glucose (i.e. in the range from about 1,000 mg/dL to about 10,000 mg/dL).

EXAMPLE 3

Direct Comparison: Change in Buffer Only

The borate formulation was compared to a formulation where the only difference in components or conditions is a change in the buffer component.

|  | Borate Formulation | Citrate Formulation |
| --- | --- | --- |
| PVP-K90 | 0.15 gm | 0.15 gm |
| GO | 50,000 U | 50,000 U |
| POD | 24,000 U | 24,000 U |
| KI | 0.6 gm | 0.6 gm |
| Sarkosyl ® | 0.1 mL | 0.1 mL |
| Boric acid (1M, pH 8.7 with sodium hydroxide) | 14 mL | — |
| Citric acid.H₂O | — | 0.65 gm |
| Sodium citrate.2H₂O | — | 3.2 gm |
| Water | qs 20 mL | qs 20 mL |
| pH | 8.7 | 5.5 |

The final buffer concentration of each impregnating solution was 0.7 M. Each impregnating solution was used to prepare glucose test devices in the same manner as described in Example 1. Devices so prepared were compared by dipping in aqueous solutions containing high concentrations of glucose, reading on MacBeth 1500 colorimeter (Kollmorgen Corp., Newburgh, N.Y.) and calculating the ΔE between the concentration read and the closest higher glucose concentration level read.

| glucose concentration | ΔE between levels citrate | borate |
|---|---|---|
| negative | | |
| | −51 | −25 |
| 1,000 mg/dL | | |
| | −1 | −14 |
| 2,000 mg/dL | | |
| | −3 | −12 |
| 3,000 mg/dL | | |
| | −1 | −13 |
| 5,000 mg/dL | | |
| | −0 | −12 |
| 10,000 mg/dL | | |
| read time | 120 sec. | 120 sec. |

The ΔE value between concentration levels indicates that the borate formulation is much superior to the citrate formulation for determination of high range glucose, i.e., the concentration range from about 1,000 mg/dL to about 10,000 mg/dL.

EXAMPLE 4

Comparison to Early Boric Acid Formulation

The glucose oxidase/peroxidase formulation in which boric acid was used as filler (Example II of U.S. Pat. Nos. 2,912,309 and 2,848,308) was used as a test composition for impregnation into carrier matrix. Devices so prepared were tested for response to high range glucose concentrations.

| POD | 5 mg |
|---|---|
| GO | 200 mg |
| o-tolidine dihydrochloride | 200 mg |
| boric acid | 1600 mg |
| water | 25 mL |

An attempt was made to dissolve the composition of the '308 and '309 patents to form an aqueous impregnating solution. The resulting solution had a pH of 2.5 and the boric acid was not completely dissolved. Nevertheless, the solution was used to impregnate a piece of Whatman 54 paper. The impregnated paper was dried at 50° C. for 20 minutes. Test devices were prepared as discussed previously.

The devices were dipped into urine containing negative, 1,000, 2,000, 4,000 and 8,000 mg/dL glucose. The ΔE values were recorded with a MacBeth 1500 colorimeter 60 seconds after contacting the sample (at longer read times the colors darken and the ΔE values are lower).

| glucose | ΔE |
|---|---|
| negative | |
| | −10 |
| 1,000 mg/dL | |
| | −1 |

| glucose | ΔE |
|---|---|
| 2,000 mg/dL | |
| | −1 |
| 4,000 mg/dL | |
| | −0 |
| 8,000 mg/dL | |

It is apparent that prior formulations using boric acid at a low pH as a "filler" failed to provide a test composition capable of distinguishing high concentration levels of glucose in aqueous test samples.

EXAMPLE 5

Pretreated Paper

Whatman 54 filter paper was pretreated, prior to incorporation with the test composition, with an aqueous solution of 0.2 M phenylboronic acid buffer (pH 9.5). The dried pretreated paper was then dipped in an impregnating solution containing:

| Borate buffer (0.8M, pH 9.5) | 5 mL |
|---|---|
| GO (12,500 U/mL) | 0.6 mL |
| POD (6,800 U/mL) | 1.0 mL |
| DHSA (0.5 M) | 1.0 mL |
| 4-aminoantipyrine (1M) | 0.25 mL |
| FC&D #5 yellow dye (1.68%) | 0.3 mL |
| Water | qs. 10.0 mL |

Test devices so prepared responded to urine glucose concentrations in the range of 500 mg/dL to 10,000 mg/dL. The yellow dye is added to obviate color interference from some highly colored clinical urines. It is not a chromogen in the system and has no affect on the visual resolution between glucose concentration levels. The color of the test device changes from yellow (negative) to brown and then to red as the glucose concentration increases. Visual resolution between negative, 500, 1,000, 2,000, 3,000 and 5,000 mg/dL glucose is good with the detectable colorimetric response forming in about 45 to 60 seconds.

EXAMPLE 6

Polymer Film

A test device responsive to from about 500 mg/dL to about 10,000 mg/dL glucose in aqueous test samples can be prepared with a polymer film incorporated with the test composition. One possible formulation is given below:

| Part A | |
|---|---|
| Potassium borate 1M, pH 9.5 | 54 gm |
| dispersing agent | 0.23 gm |
| pigment | 7.0 gm |
| defoamer | 0.007 gm |
| surfactant | 0.20 gm |
| thickener | 0.62 gm |
| Part B | |
| Potassium borate 1M, pH 9.5 | 4.5 mL |
| GO (5000 U/mL) | 0.44 mL |
| POD (4000 U/mL) | 0.4 mL |
| PVP-K90 | 0.6 gm |
| KI | 1.0 gm |
| Part C | |

| | |
|---|---|
| Poly (ST-Co-MMA) dispersion (42% styrene) | 0.85 gm |

Mix Parts A & B with stirring. When a uniform paste is obtained, carefully add Part C under mild mixing conditions to prevent coagulation. The final polymer suspension obtained is applied to a plastic backing such as Trycite ® (polystyrene) and is dried in an air oven at 50° C. for 20 minutes.

Test devices prepared in this fashion are expected to respond to high range urine glucose concentrations (i.e., in the range of from about 500 mg/dL to about 10,000 mg/dL).

Obviously, many modifications and variations of the invention as set forth may be made without departing from the spirit or scope of the invention.

What is claimed is:

1. A test composition for the semiquantitative determination of high range glucose in an aqueous test sample, comprising; glucose oxidase, a peroxidatively active component, a chromogenic indicator system capable of providing a detectable colorimetric response and a borate buffer capable of providing an initial pH above about pH 7.

2. The test composition of claim 1 in which the borate buffer is a boric acid buffer or a phenylboronic acid buffer.

3. The test composition of claim 2 in which the borate buffer is a boric acid buffer and the chromogenic indicator system is a water soluble iodide salt and a poly(-vinylpyrrolidone).

4. The test composition of claim 3 in which the boric acid buffer is capable of providing an initial pH between about pH 8.5 and about pH 9.5.

5. A test device for the semiquantitative determination of high range glucose in an aqueous fluid sample comprising:
(a) a carrier matrix, and
(b) a test composition incorporated therewith, the test composition including glucose oxidase, a peroxidatively active component, a chromogenic indicator system capable of providing a detectable response and a borate buffer capable of providing an initial pH above about pH 7.

6. The test device of claim 5 in which the borate buffer is a boric acid buffer or a phenylboronic acid buffer.

7. The test device of claim 6 in which the borate buffer is a boric acid buffer and the chromogenic indicator system is a water soluble iodide salt and poly(vinylpyrrolidone).

8. The test device of claim 7 in which the boric acid buffer is capable of providing an initial pH is between about pH 8.5 and about pH 9.5.

9. A method of preparing the test device for the semiquantitative determination of high range glucose in an aqueous test sample, comprising the steps of:
(a) incorporating with a carrier matrix with a test composition including glucose oxidase, a peroxidatively active component, a chromogenic indicator system capable of providing a detectable response and from about 0.2 M to about 0.8 M borate buffer capable of providing an initial pH above about 7; and
(b) drying.

10. The method of claim 9 in which the borate buffer is a boric acid buffer and the chromogenic indicator system is a water soluble iodide salt and a poly(vinylpyrrolidone).

11. The method of claim 10 in which the boric acid buffer is capable of providing an initial pH between about pH 8.5 and about pH 9.5.

12. The method of claim 9 in which the carrier matrix is paper and the method includes the additional step of pretreating the paper matrix with a borate buffer at an initial pH about 7 prior to incorporating the matrix with the test composition.

* * * * *